(12) United States Patent
Pfeiffer et al.

(10) Patent No.: US 9,498,267 B2
(45) Date of Patent: Nov. 22, 2016

(54) BONE PLATE

(75) Inventors: Sven Pfeiffer, Königsee (DE); Christian Krüger, Bad Blankenburg (DE); Thomas Schlegel, Königsee (DE)

(73) Assignee: KÖNIGSEE IMPLANTATE GMBH, Allendorf OT Aschau (DE)

( * ) Notice: Subject to any disclaimer, the term of this patent is extended or adjusted under 35 U.S.C. 154(b) by 425 days.

(21) Appl. No.: 14/347,110

(22) PCT Filed: Aug. 30, 2012

(86) PCT No.: PCT/EP2012/066906
§ 371 (c)(1),
(2), (4) Date: Jun. 30, 2014

(87) PCT Pub. No.: WO2013/053539
PCT Pub. Date: Apr. 18, 2013

(65) Prior Publication Data
US 2014/0316473 A1  Oct. 23, 2014

(30) Foreign Application Priority Data
Oct. 14, 2011 (DE) .................... 20 2011 106 835 U

(51) Int. Cl.
*A61B 17/80* (2006.01)

(52) U.S. Cl.
CPC ....... *A61B 17/8057* (2013.01); *A61B 17/8014* (2013.01)

(58) Field of Classification Search
None
See application file for complete search history.

(56) References Cited

U.S. PATENT DOCUMENTS

| 6,669,701 | B2 | 12/2003 | Steiner et al. ................ 606/69 |
| 8,323,321 | B2 | 12/2012 | Gradl ........................... 606/291 |
| 2007/0093836 | A1 | 4/2007 | Derouet ......................... 606/69 |
| 2008/0119894 | A1 | 5/2008 | Ehrhardt et al. .............. 606/280 |
| 2009/0024172 | A1* | 1/2009 | Pizzicara ........... A61B 17/8057 606/280 |

FOREIGN PATENT DOCUMENTS

| DE | 10 2005 004 841 | 7/2006 | ............. A61B 17/58 |
| DE | 10 2006 000 948 | 10/2006 | ............. A61B 17/58 |

(Continued)

OTHER PUBLICATIONS

Each of the International Search Report (in English), dated Apr. 12, 2012, the Written Opinion of the International Searching Authority (in English), dated Apr. 14, 2014, and the International Preliminary Report on Patentability (in English), dated Apr. 15, 2014, which issued from the ISA/European Patent Office for corresponding PCT Application No. PCT/EP2012/066906, filed on Aug. 30, 2012, each from the World Intellectual Property Organization (WIPO) is enclosed.

*Primary Examiner* — Sameh Boles
(74) *Attorney, Agent, or Firm* — Gerald T. Bodner

(57) ABSTRACT

The invention relates to a bone plate (1), comprising a bottom side (4) intended for lying against the bone, a top side (3) facing away from the bone, a plurality of holes that penetrate the plate, of which holes at least one hole is used to accommodate a bone screw that has or does not have a threaded screw head, wherein furthermore at least one of the holes has a spherical oblong-hole shape having a threaded section. According to the invention, the at least one oblong hole has a thread having at least one thread turn on the overall inner peripheral side, wherein the at least one thread turn is not interrupted in a first pitch circle region (A) and is interrupted by thread-free recesses (6) in a second pitch circle region (B) and furthermore the thread has a conical shape in the first pitch circle region and the thread extends from the plate bottom side to the spherical formation in the second pitch circle region, wherein the section of the spherical recess extending to the plate top side is likewise thread-free.

10 Claims, 2 Drawing Sheets

(56) References Cited

FOREIGN PATENT DOCUMENTS

| DE | 10 2005 042 766 | 1/2007 | ............. A61B 17/58 |
| DE | 10 2008 043 370 | 5/2010 | ............. A61B 17/58 |
| EP | 1 712 197 | 10/2006 | ............. A61B 17/80 |
| EP | 2 016 918 | 1/2009 | ............. A61B 17/80 |
| WO | WO 0 154 601 | 8/2001 | ............. A61B 17/56 |
| WO | WO 2011/032140 | 3/2011 | ............. A61B 17/80 |

* cited by examiner

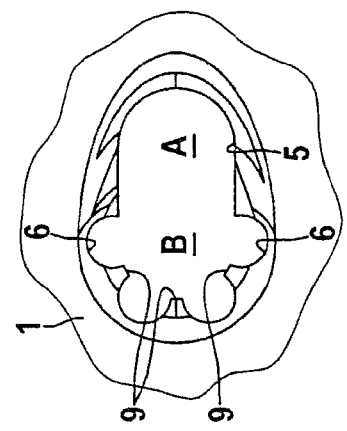
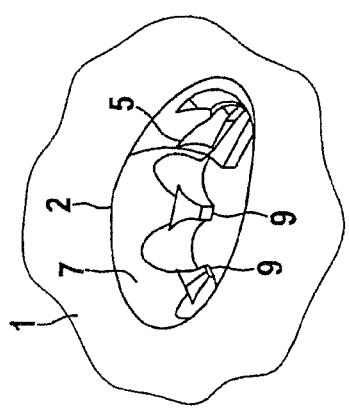
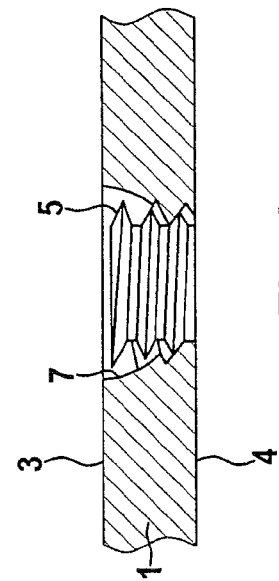
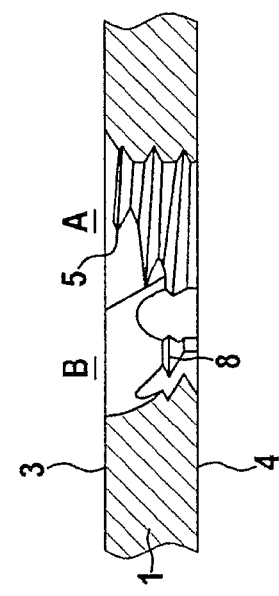

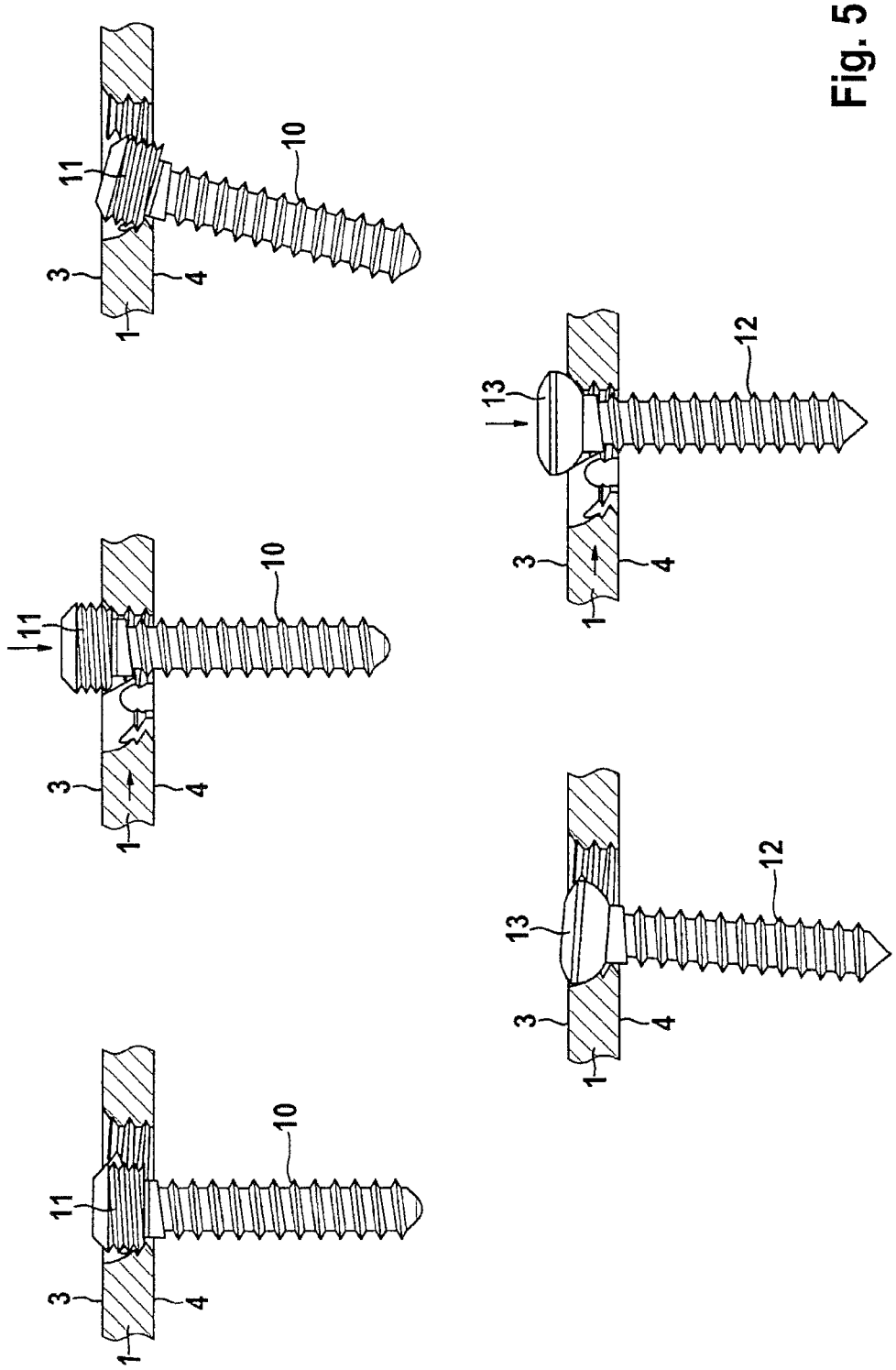

BONE PLATE

The invention relates to a bone plate comprising a bottom side intended for lying against the bone and a top side facing away from the bone, a plurality of holes penetrating the plate, of which holes at least one hole serves to accommodate a bone screw with or without a threaded screw head, and wherein further at least one of the holes has a spherical oblong hole shape with a threaded section, according to claim 1.

A bone plate having a top side and a bottom side is already known from PCT WO 01/54601 A1, with multiple holes arranged along the longitudinal axis of the plate and connecting the top side to the bottom side being provided to accommodate bone screws. At least one of the holes is formed of a combination of a circular hole having a predefined diameter and a center of symmetry and an oblong hole having another center of symmetry, which has a long axis running in the direction of the longitudinal axis of the plate and a short axis running vertically to the long axis.

The bone plate is to permit a use as a compression plate and a so-called internal fixative. The circular hole according to the solution of PCT WO 01/54601 A1 has an internal thread structure, so that a bone screw with a complementary threaded head can be accommodated. The further, joining portion of the oblong hole is spherical, but thread-free.

The bone plate according to WO 2011/032140 A1, too, includes a number of holes having the design similar to an oblong hole, the oblong holes having a constricted portion and being formed of two pitch circles. A first pitch circle has a spherical shape towards the top side of the plate, and is joined by a second pitch circle having a design with a discontinued thread. The bone plate in question is to be usable also as a so-called compression plate.

In the bone plate according to EP 1 712 197 A1, too, holes connecting the top side and the bottom side of the plate are provided along the longitudinal axis of the plate, wherein at least one of the holes is configured as a continuous oblong hole. The longer axis of the oblong hole shows in the direction of the longitudinal axis of the plate. The oblong hole, facing the top side, includes a guide structure for accommodating a screw head of the bone screw. On one portion of the inner circumference of the oblong hole a holding structure is formed for locating a screw head or a screw neck of a bone screw, which defines a longitudinal axis. The holding structure has a bearing line for the screw head or screw neck in a plane of its longitudinal axis, said bearing line being described by a second or higher degree function. Preferably, the bearing line is a pitch circular bearing line.

In the bone plate according to DE 10 2006 000 948 A1 the holes are formed as oblong holes having a length L and a radius R. In one portion of the inner circumference of the oblong hole a thread is incorporated whose longitudinal axis is inclined towards the longitudinal axis of the plate with respect to the horizontal formed by the bone plate. The through hole may also be elliptical, and it is possible to configure the internal thread as an oval or spherical thread. Such an oblong hole is to realize a compression from both sides. In one embodiment, the inclination of the longitudinal axis of the thread is between 90° and 45°.

Based on the foregoing it is the object of the invention to provide further developed bone plate comprising a bottom side intended for lying against the bone and a top side facing away from the bone and a plurality of holes penetrating the plate, wherein the further developed bone plate may be used multifunctionally through the use of both standard bone screws having a thread-free screw head and bone screws having a head with a spherical or conical thread, so that different attachment possibilities, including the compression of bone fragments can be realized. The bone plate to be created is intended for the reduction of a plurality of plates for different application purposes which would otherwise have to be kept in stock.

The solution to the object of the invention is achieved by a bone plate according to the feature combination of claim 1. The dependent claims describe at least useful embodiments and further developments.

Accordingly, there is proposed a bone plate comprising a bottom side intended for lying against the bone and a top side facing away from the bone and a plurality of holes penetrating the plate. At least one of the holes is suited to accommodate a bone screw with or without a threaded screw head. Further, at least one of the holes has a spherical oblong hole shape with a threaded section.

According to the invention the at least one oblong hole is provided with a thread on the entire internal circumference, the thread comprising at least one thread turn, wherein the at least one thread turn is not discontinued in a first pitch circle region and is discontinued by thread-free recesses in a second pitch circle region.

The thread in the first pitch circle region has a conical or conical-spherical shape. The thread in the second pitch circle region is configured to extend from the bottom side of the plate up to the spherical recess into this pitch circle region, wherein the section of the spherical recess extending to the top side of the plate is thread-free as well.

In a preferred embodiment of the invention the thread in the second pitch circle region is conical.

Viewed from the top side of the plate the diameter of the second pitch circle region is greater than that of the first pitch circle region.

The thread-free recesses, again, can be configured as pitch circles, wherein tooth-like segments carrying the thread remain between these pitch circles.

The shape and the depth of the spherical recess substantially correspond to the head height of a bone screw having a spherical head, so that same is almost flush with the top side of the plate in the fully screwed in state.

The at least one hole having the shape of an oblong hole is configured as a combination hole for the bone fragment compression as well as for the variable-angle or fixed-angle fixing by means of cortical bone screws.

The diameter of the aforementioned recess pitch circles is respectively smaller than half the diameter of the second pitch circle region, viewed from the bottom side of the plate.

The longitudinal axis of the at least one oblong hole substantially extends on the longitudinal axis of the bone plate, or is parallel to same. In one embodiment of the invention the longitudinal axis of the oblong hole deviates from the parallel position relative to the longitudinal axis by an angle amounting to some degrees.

According to the invention the thread may be an impression in the form of a three-dimensional structure, wherein the impression merely approximates the form of the thread. In such an embodiment a quasi preformed thread is provided which receives its final structure and contour only when a bone screw having a corresponding conical or spherical thread in the threaded head is screwed in to obtain a fixed-angle position. This measure increases the stability of the respective bone screw without risking that the screw breaks when it is unscrewed later after the bone fracture(s) has/have healed.

In one embodiment the thread in the first pitch circle region extends with reference to the assumed center thereof substantially over 300° to 320° and runs symmetrically with respect to the longitudinal axis of the plate.

The above-described bone plate allows to ensure a fixed-angle connection when using bone screws with a threaded screw head. If a screw having a spherical threaded screw head in screwed into the threaded section in the first pitch circle region a compressing effect is obtained by a corresponding relative movement between the bone fragment and the bone plate. At the same time, a fixed-angle position is obtained. If a bone screw having a threaded head is introduced in the region of the second pitch circle and the thread turn discontinued there a variable fixed-angle connection can be realized.

If a standard cortical bone screw having a spherical head is inserted, same may be introduced in an optional variable-angle manner. Also, for the purpose of compressing bone fragments, it may be introduced and fixed by screwing in the region of the first pitch circle section.

The invention will be explained in more detail below by means of an exemplary embodiment and with reference to the figures.

In the figures:

FIG. 1 shows a perspective top view of an oblong hole provided with a thread on the entire internal circumference according to the invention;

FIG. 2 shows a top view of an oblong hole with a thread formed on the entire internal circumference according to the invention;

FIG. 3 shows a longitudinal section through the oblong hole according to the invention;

FIG. 4 shows a cross-section through the oblong hole according to the invention;

FIG. 5 shows various illustrations of different application possibilities using the bone plate according to the invention either with cortical screws that have a threaded head, or standard cortical screws with a spherical head.

The bone plate 1, of which only a section is shown in the figures, comprises at least one oblong hole according to the invention, which is configured as a so-called combination hole 2.

This oblong hole extends from the top side 3 of the plate 1 to the bottom side 4 thereof.

If is also possible, of course, to provide other holes in plate 1 which are not covered by the invention, for example, drainage holes, holes for receiving guide wires or a drilling template.

The shape of the bottom side of the plate may deviate from the plane form and have, for example in a cross-sectional view, a bent shape so as to support the growth of the bone underneath the plate.

As can be seen in FIG. 1, the oblong hole 2 has a spherical form corresponding to the top side of the plate 3.

The oblong hole according to the invention has a thread on the entire internal circumference, as can be seen in the longitudinal section according to FIG. 3.

In a first pitch circle region A (see FIG. 2) the at least one thread turn 5 is not discontinued.

In a second pitch circle region B the thread turn is discontinued, namely by thread-free recesses 6.

The thread in the first pitch circle region A has a conical shape (see FIG. 3). The thread in the second pitch circle region B extends from the bottom side 4 of the plate up to the spherical recess 7, with the section of the spherical recess extending to the top side of the plate, too, being without a thread so as to receive a standard cortical screw having a spherical head in an almost flush manner (see illustration according to FIG. 5 at the lower left).

The thread 8 of the second pitch circle region B, too, may have a conical shape. Viewed from the top side 3 of the plate the diameter of the second pitch circle region B is greater than the diameter of the first pitch circle region A.

The thread-free recesses 6 are configured as pitch circles. Tooth-shaped segments 9 carrying the thread remain between these pitch circles.

The at least one hole is configured as an oblong hole within the meaning of a combination hole, for the bone fragment compression and for the fixed-angle or variable-angle fixing by means of cortical bone screws (see FIG. 5).

The diameter of the recess pitch circles in the thread-free section 6 is, in one embodiment, smaller than half the diameter of the second pitch circle region B, viewed from the bottom side of the plate.

The longitudinal axis of the oblong hole substantially extends on the longitudinal axis of the bone plate, or is parallel to same. Also, predetermined angle deviations in the range of 1° to 10° are advantageous in selected applications.

In a preferred embodiment of the invention the thread provided on the entire internal circumference is configured as a three-dimensional structure which approximates a thread form. The structure may consist of micro elevations and recesses. Such a microstructuring of an approximated thread allows, on the one hand, the easy accommodation of a screw having a threaded head. On the other hand, such an embodiment of the thread brings about a safe support of the corresponding cortical screw having a threaded head in that the cut of the thread is quasi completed by the cutting effect of the threaded screw head, with due regard to an adapted hardness between the plate material and the bone screw material. An undesired detachment of a cortical screw of this type is effectively prevented. At the same time, the screw head is prevented from being torn off when the screws are removed.

The thread in the first pitch circle region extends with reference to the assumed center thereof substantially over 300° to 320° and runs symmetrically with respect to the longitudinal axis of the plate, respectively long axis of the oblong hole.

Different attachment possibilities and applications of the bone plate are now introduced with reference to FIG. 5. It is possible to realize a standard screw connection, a standard screw connection with compression, a fixed-angle screw connection, a variable fixed-angle screw connection, and also a fixed-angle screw connection with compression in the oval compression portion of the hole.

In FIG. 5, upper row of the illustrations from left to right, a fixed-angle connection is shown on the left. A bone screw 10 having threaded head 11 is screwed in in the region of the second pitch circle B (see FIG. 2).

In the illustration shown in the middle of FIG. 5, upper row, the same bone screw 10 having a threaded screw head 11 is screwed into the pitch circle region A. Upon screwing it in (vertical arrow) the bone plate 1 moves in the direction of the arrow (horizontal arrow), resulting in a desired compression of the respective bone fragments (not shown).

In the illustration shown at the top on the right of FIG. 5, a bone screw 10 having a threaded screw head 11 is screwed into the pitch circle region B in a variable-angle manner, and a variable-angle fixing can be realized accordingly.

With regard to the mode of operation of variable fixed-angle star holes and fixed-angle combined compression holes reference is made to the patents in the name of the applicant, DE 10 2005 042 766 B4 and DE 10 2005 004 841 B4, to the full content of which reference is herewith being made.

In the drawing sequence of FIG. 5, at the lower left, a standard cortical screw 12 having a spherical head 13 is screwed into the second pitch circle region B, which is almost flush due to the spherical shape 7.

If compression is desired, it is possible to introduce the aforementioned standard screw 12 having a spherical, thread-free head 13 into the first pitch circle region A. The driving in of the screw in the direction of the arrow (vertical arrow) then results in a relative movement between the screw 12 and the bone plate 1 in the direction of the arrow (horizontal arrow).

The invention claimed is:

1. Bone plate comprising a bottom side intended for lying against the bone and a top side facing away from the bone, a plurality of holes penetrating the plate, of which holes at least one hole serves to accommodate a bone screw with or without a threaded screw head, and wherein further at least one of the holes has a spherical oblong hole shape with a threaded section,
characterized in that
the at least one oblong hole is provided with a thread on the entire internal circumference, the thread comprising at least one thread turn, wherein the at least one thread turn is not discontinued in a first pitch circle region and is discontinued by thread-free recesses in a second pitch circle region, further the thread in the first pitch circle region has a conical shape and the thread in the second pitch circle region extends from the bottom side of the plate up to the spherical recess, wherein the section of the spherical recess extending to the top side of the plate is thread-free as well.

2. Bone plate according to claim 1,
characterized in that
the thread in the second pitch circle region is conical.

3. Bone plate according to claim 1,
characterized in that
viewed from the top side of the plate the diameter of the second pitch circle region is greater than that of the first pitch circle region.

4. Bone plate according to claim 1,
characterized in that
the thread-free recesses are configured as pitch circles, wherein tooth-like segments carrying the thread remain between these pitch circles.

5. Bone plate according to claim 4,
characterized in that
the diameter of the recess pitch circles is respectively smaller than half the diameter of the second pitch circle region, viewed from the bottom side of the plate.

6. Bone plate according to claim 1,
characterized in that
the form and/or the depth of the spherical recess substantially correspond(s) to the head height of a bone screw having a spherical head.

7. Bone plate according to claim 1,
characterized in that
the at least one hole having the shape of an oblong hole is configured as a combination hole for the bone fragment compression as well as for the fixed-angle or variable-angle fixing by means of cortical bone screws.

8. Bone plate according to claim 1,
characterized in that
the longitudinal axis of the oblong hole substantially extends on the longitudinal axis of the bone plate, or is parallel to same.

9. Bone plate according to claim 1,
characterized in that
the thread is an impression in the form of a three-dimensional structure which merely approximates the form of the thread.

10. Bone plate according to claim 1,
characterized in that
the thread in the first pitch circle region extends with reference to the assumed center thereof substantially over 300° to 320° and runs symmetrically with respect to the longitudinal axis of the plate.

* * * * *